US007863262B2

(12) United States Patent
Wink et al.

(10) Patent No.: US 7,863,262 B2
(45) Date of Patent: *Jan. 4, 2011

(54) NITROXYL PROGENITORS IN THE TREATMENT OF HEART FAILURE

(75) Inventors: David A. Wink, Hagerstown, MD (US); Martin Feelisch, Shreveport, LA (US); David A. Kass, Columbia, MD (US); Nazareno Paolocci, Baltimore, MD (US); Katrina Miranda, Tucson, AZ (US); Jon Fukuto, Agoura, CA (US); Tatsuo Katori, Baltimore, MD (US)

(73) Assignees: Johns Hopkins University, Baltimore, MD (US); The United States of America as represented by the Department of Health and Human Services, Washington, DC (US); The Regents of the University of California, Los Angeles, CA (US); The Board of Supervisors of Louisiana State University and Agriculture and Mechanical College, Shreveport, LA (US)

( * ) Notice: Subject to any disclaimer, the term of this patent is extended or adjusted under 35 U.S.C. 154(b) by 661 days.

This patent is subject to a terminal disclaimer.

(21) Appl. No.: 11/096,924

(22) Filed: Mar. 31, 2005

(65) Prior Publication Data
US 2005/0192254 A1 Sep. 1, 2005

Related U.S. Application Data

(63) Continuation of application No. 10/226,412, filed on Aug. 21, 2002, now Pat. No. 6,936,639.

(51) Int. Cl.
*A01N 51/00* (2006.01)
*A61K 31/655* (2006.01)
*A61K 31/13* (2006.01)
*A61K 33/26* (2006.01)

(52) U.S. Cl. .................. 514/183; 514/149; 514/611
(58) Field of Classification Search .......... 514/183, 514/149, 611
See application file for complete search history.

(56) References Cited

U.S. PATENT DOCUMENTS

| 4,539,321 A | * | 9/1985 | Campbell ............... 514/252.03 |
| 4,954,526 A | | 9/1990 | Keefer |
| 5,039,705 A | | 8/1991 | Keefer et al. |
| 5,212,204 A | * | 5/1993 | Keefer et al. ............ 514/647 |
| 5,789,447 A | | 8/1998 | Wink, Jr. et al. |
| 5,814,656 A | | 9/1998 | Saavedra et al. |
| 6,083,515 A | | 7/2000 | Garvey et al. |
| 6,143,734 A | | 11/2000 | Garvey et al. |
| RE37,116 E | | 3/2001 | Garvey et al. |
| 6,297,260 B1 | | 10/2001 | Bandarage et al. |
| 6,323,234 B1 | | 11/2001 | Garvey et al. |
| 6,936,639 B2 | | 8/2005 | Wink et al. |
| 2002/0010146 A1 | | 1/2002 | Garvey et al. |
| 2002/0016322 A1 | | 2/2002 | Bandarage et al. |
| 2002/0119977 A1 | | 8/2002 | Kanapure et al. |
| 2004/0038947 A1 | | 2/2004 | Wink et al. |

FOREIGN PATENT DOCUMENTS

| WO | WO 96/32946 | 4/1996 |
| WO | WO 98/43621 | 3/1998 |
| WO | WO 99/33823 | 7/1999 |
| WO | WO-00/28988 A1 | 5/2000 |
| WO | WO 00/67754 | 11/2000 |
| WO | WO 01/45703 | 6/2001 |
| WO | WO 02/060378 | 8/2002 |
| WO | WO-2005/074598 A2 | 8/2005 |
| WO | WO-2005/074598 A3 | 8/2005 |

OTHER PUBLICATIONS

Maragos et. al., J. Med. Chem (1991) 34:3242-3247.*
Paolocci et. al. (PNAS (2001) 98:10463-10468).*
Remme et. al. (European Heart Journal (2001) 22:1527-1560).*
Advisory Action mailed May 25, 2007, for U.S. Appl. No. 10/463,084, filed Jun. 16, 2003, 3 pages (3.00).
Amendment in Response to Final Office Action mailed May 8, 2007, for U.S. Appl. No. 10/463,084, filed Jun. 16, 2003, 13 pages.
Final Office Action mailed Mar. 8, 2007, for U.S. Appl. No. 10/463,084, filed Jun. 16, 2003, 7 pages.
Fukuto, J.M. (2005). "Nitroxyl (HNO): Chemistry, Biochemistry, and Pharmacology," *Annu. Rev. Pharmacol Toxicol.* 45:335-355.
Fukuto, J.M. et al. (Apr. 2005). "The Chemistry and Biology of Nitroxyl (HNO): A Chemically Unique Species with Novel and Important Biological Activity," *Chembiochem.* 6:612-619.
Miranda, K.M. (2005). "Donors of HNO," *Curr. Top. Med. Chem.* 5(7):649-664.
Pagliaro, P. (2003). "Differential Biological Effects of Products of Nitric Oxide (NO) Synthase: It is Not Enough to Say NO," *Life Sci.* 73:2137-2149.

(Continued)

*Primary Examiner*—Brandon J Fetterolf
*Assistant Examiner*—Marcos Sznaidman
(74) *Attorney, Agent, or Firm*—Arnold & Porter LLP

(57) ABSTRACT

Administration of an HNO/NO⁻ donating compound, such as Angeli's salt, increases myocardial contractility while concomitantly lowering left ventricular preload in subjects experiencing heart failure. Moreover, administration of the HNO/NO⁻ donating compound isopropylamine (IPA)/NO(Na(CH₃)₂CHNHN(O)NO) surprisingly exhibited positive inotropic effects in subjects experiencing heart failure that were superior to those caused by the HNO/NO⁻ donating compound Angeli's salt. Additionally, in contrast to the effects observed with NO⁻ donors, administration of an HNO/NO⁻ donor in combination with a positive inotropic agent did not impair the positive inotropic effect of the positive inotropic agent. Further, HNO/NO⁻ exerts its positive inotropic effect independent of the adrenergic system, increasing contractility even in subjects receiving beta-antagonist therapy.

18 Claims, 8 Drawing Sheets

OTHER PUBLICATIONS

Pagliaro, P. (2003). "Nitroxyl Affords Thiol-Sensitive Myocardial Protective Effects Akin to Early Preconditioning," *Free Radic. Biol. Med.* 34(1):33-43.

Paolocci, N. (Apr. 29, 2003). "Positive Inotropic and Lusitropic Effects of HNO/NO⁻in Failing Hearts: Independence from β-Adrenergic Signaling," *PNAS* 100(9):5534-5542.

Paolocci, N. et al. (Feb. 2007; e-pub. Nov. 29, 2006). "The Pharmacology of Nitroxyl (HNO) and its Therapeutic Potential: Not Just the Janus Face of NO," *Pharmacology and Therapeutics* 113(2): 442-458.

Thomas, D.D. (2002), "Guide for the Use of Nitric Oxide (NO) Donors as Probes of the Chemistry of NO and Related Redox Species in Biological Systems," Chapter 8, *in Nitric Oxide, Part D: Nitric Oxide Detection, Mitochondria and Cell Functions, and Peroxynitrite Reactions*, Academic Press: Amsterdam, pp. 84-105.

U.S. Appl. No. 10/587,644, filed Jul. 27, 2006, by Toscano et al.

U.S. Appl. No. 11/922,793, filed Dec. 21, 2007, by Paolocci et al.

Wink, D.A. et al. (Dec. 2003; first published Jul. 10, 2003). "Orthogonal Properties of the Redox Siblings Nitroxyl and Nitric Oxide in the Cardiovascular System: a Novel Redox Paradigm," *Am. J. Physiol. Heart Circ. Physiol.* 285:H2264-H2276.

Fitzhugh et al., *Free Radical Biology & Medicine*, vol. 28, No. 10, pp. 1463-1469 (2000).

Harrison's Principles of Internal Medicine, Isselbacher et al., eds., 13th ed. vol. 1, 1994, pp. 1002-1008.

Hart et al., Abstract, *Am J Physiol Heart Circ Physiol*, vol. 281, No. 1, pp. H146-H154 (Jul. 2001).

Ma et al., *PNAS*, vol. 96, No. 25, pp. 14617-14622 (1999).

Maragos et al., *J. Med. Chem.*, vol. 34, No. 11, pp. 3242-3247 (1991).

Pagliaro et al., Abstract 1265, *Supplement to Circulation*, vol. 104, No. 17, pp. 11-263-11-264 (2001).

Pagliaro et al., *J. Physiol.*, vol. 536, p. 143P (2001).

Paolocci et al., Abstract, *Italian Heart Journal*, vol. 2, Suppl. 3, p. 62S (Sep. 2001).

Paolocci et al., *PNAS*, vol. 98, No. 18, pp. 10463-10468 (Aug. 28, 2001).

De Witt, B.J. et al. (Nov. 2, 2001). "Comparison of Responses to Novel Nitric Oxide Donors in the Feline Pulmonary Vascular Bed," *Eur. J. Phramacol.* 430(2-3):311-315.

Fukuto, J.M. et al. (Nov. 1992). "The Pharmacological Activity of Nitroxyl: A Potent Vasodilator with Activity Similar to Nitric Oxide and/or Endothelium-Derived Relaxing Factor," *J. Pharmacol. Exp. Ther.* 263(2):546-551.

Gelvan, D. et al. (Jun. 1, 1991). "Cardiac Reperfusion Damage Prevented by a Nitroxide Free Radical," *Proc. Natl. Acad. Sci. USA* 88(1):4680-4684.

Li, H. et al. (Apr. 15, 2002). "Polynitroxyl-Albumin (PNA) Enhances Myocardial Infarction Therapeutic Effect of Tempol in Rat Hearts Subjected to Regional Ischemia-Reperfusion," *Free Radic. Biol. Med.* 32(8):712-719.

Naughton, P. et al. (2001). "Induction of Haem Oxygenase-1 by Nitroxyl Anion (NO⁻) in Cardiomyocytes," *J. Physiol* 531:194P.

Pagliaro, P. et al. (2001). "Is Nitroxyl Anion Involved in Myocardial Protection Against Ischaemia/Reperfusion Injury in Isolated Rat Hearts?" *J. Physiol.* 536:143P.

Pagliaro, P. et al. (2001). "Nitroxyl Anion is a Preconditioning Agent in Isolated Rat Heart," *Circulation* 104(17 Suppl.):II-263-II-264, Abstract 1265.

Paolocci, N. et al. (Sep. 2001). "Nitroxyl Anion Improves In Vivo Contractile Function and Promotes Active Relaxation in Experimental Heart Failure," *Italian Heart Journal* 2(Suppl. 3):62S, Abstract No. 38.

Takahira, R. et al. (Sep. 15, 2001). "Dexamethasone Attenuates Neutrophil Infiltration in the Rat Kidney in Ischemia/Reperfusion Injury: The Possible Role of Nitroxyl," *Free Radic. Biol. Med.* 31(6):809-815.

Tosaki, A. et al. (Nov.-Dec. 1992). "Does the Antiarrhythmic Effect of DMPO Originate from its Oxygen Radical Trapping Property or the Structure of the Molecule Itself?" *Basic Res. Cardiol.* 87(6):536-547.

Vanuffelen, B.E. et al. (Mar. 1, 1998). "Intracellular but not Extracellular Conversion of Nitroxyl Anion into Nitric Oxide Leads to Stimulation of Human Neutrophil Migration," *Biochem. J.* 330(Pt. 2) :719-722.

Yu, L. et al. (Mar. 1, 1994). "Nitric Oxide: A Mediator in Rat Tubular Hypoxia/Reoxygenation Injury," *Proc. Natl. Acad. Sci. USA* 91(5):1691-1695.

Bassani, R.A. et al. (Oct. 1994). "Na-Ca Exchange is Required for Rest-decay but not for Rest-potentiation of Twitches in Rabbit and Rat Ventricular Myocytes," *J. Mol. Cell. Cardiol.* 26(10):1335-1347.

Bristow, M.R. (2000). "β-Adrenergic Receptor Blockade in Chronic Heart Failure," *Circulation* 101:558-569.

The Canadian Cardiovascular Society. (2001). "The 2001 Canadian Cardiovascular Society Consensus Guideline Update for the Management and Prevention of Heart Failure," twenty-eight pages.

Chavey II, W.E. et al. (Sep. 15, 2001). "Guideline for the Management of Heart Failure Caused by Systolic Dysfunction: Part II. Treatment," *American Family Physician* 64(6):1045-1054.

Cheng, H. et al. (Feb. 1999). "Amplitude Distribution of Calcium Sparks in Confocal Images: Theory and Studies with an Automatic Detection Method," *Biophys. J.* 76(2):606-617.

Cheong, E. et al. (Jan. 2005). "Nitroxyl Triggers $Ca^{2+}$Release from Skeletal and Cardiac Sarcoplasmic Reticulum by Oxidizing Ryanodine Receptors," *Cell Calcium* 37(1):87-96.

Colton, C.A. et al. (Sep. 2001). "Nitroxyl Anion Regulation of the NMDA Receptor," *J. Neurochem.* 78(5):1126-1134.

Colucci, W.S. et al. (2009). "Treatment of Acute Decompensated Heart Failure," located at <http://www.utdol.com.ezproxy.welch.hjmi.edu/online/content/topic.do?to...> last visited on Aug. 10, 2009, twenty-six pages.

Cortassa, S. et al. (Sep. 2004). "A Mitochondrial Oscillator Dependent on Reactive Oxygen Species," *Biophys. J.* 87(3):2060-2073.

Diaz, M.E. et al. (Sep.-Oct. 2005). "The Control of Sarcoplasmic Reticulum Ca Content in Cardiac Muscle," *Cell Calcium* 38(3-4):391-396.

Didomenico, R.J. at al. (Apr. 2004, e-published Feb. 24, 2004). "Guidelines for Acute Decompensated Heart Failure Treatment," *The Annuals of Pharmacotherapy* 38:649-660.

Dostal, D.E. et al. (Oct. 1992). "Detection of Angiotensin I and II in Cultured Rat Cardiac Myocytes and Fibroblasts," *Am. J. Physiol.* 263(4-Pt. 1):C851-C863.

Feelisch, M. (Apr. 29, 2003; e-pub. Apr. 18, 2003). "Nitroxyl Gets to the Heart of the Matter," *Proc. Natl. Acad. Sci. USA* 100(9):4978-4930.

Felker, G.M. et al. (Mar. 19, 2003). "Heart Failure Etiology and Response to Milrinone in Decompensated Heart Failure," *JACC* 41(6):997-1003.

Felker, G.M. et al. (Dec. 2004). "Risk Stratification After Hospitalization for Decompensated Heart Failure," *Journal of Cardiac Failure* 10(6):460-466.

Feld, Y. et al. (2006). "Future Strategies for the Treatment of Diastolic Heart Failure," *Acute Card. Care* 8(1):13-20.

Franklin, K.M. et al. (Mar.-Apr. 2005). "Prognosis in Diastolic Heart Failure," *Prog. Cardiovasc. Dis.* 47(5):333-339.

Froehlich, J.P. et al. (1978). "Studies of Sarcoplasmic Reticulum Function and Contraction Duration in Young Adult and Aged Rat Myocardium," *J. Mol. Cell. Cardiol.* 10(5):427-438.

Fukuto, J.M. et al. (May 2005). "The Physiological Chemistry and Biological Activity of Nitroxyl (HNO): The Neglected, Misunderstood, and Enigmatic Nitrogen Oxide," *Chem. Res. Toxicol.* 18(5):790-801.

Gheorghiade, M. et al. (2009). "Acute Heart Failure Syndromes," *Journal of the American College of Cardiology* 53(7):557-573.

Hain, J. et al. (Feb. 3, 1995). "Phosphorylation Modulates the Function of the Calcium Release Channel of Sarcoplasmic Reticulum from Cardiac Muscle," *J. Biol. Chem.* 270(5):2074-2081.

Heart Failure Society of America. (2006). "Section 1: Development and Implementation of a Comprehensive Heart Failure Practice Guideline," Heart Failure Society of America, pp. 1-95.

Heart Failure Society of America. (1999). "Heart Failure Society of America (HFSA) Practice Guidelines. HFSA Guidelines for Management of Patients With Heart Failure caused by Left Ventricular Systolic Dysfunctions—Pharmacological Approaches," Heart Failure Society of America, pp. 1-36.

Hunt, S.A. et al. (2001). "ACC/AHA Guidelines for the Evaluation and Management of Chronic Heart Failure in the Adult," *American College of Cardiology and the American Heart Association, Inc.* pp. 1-56.

International Search Report mailed on Nov. 17, 2006, for International Application No. PCT/US2006/024545 filed on Jun. 23, 2006, four pages.

Jiang, M.T. et al. (Nov. 29, 2002, e-pub. Oct. 24, 2002). "Abnormal $Ca^{2+}$Release, but Normal Ryanodine Receptors, in Canine and Human Heart Failure," *Circ. Res.* 91(11):1015-1022.

Kass, D.A. (Aug. 2000). "Assessment of Diastolic Dysfunction: Invasive Modalities," *Cardiol. Clin.* 18(3):571-586.

Kass, D.A. et al. (Jun. 25, 2004). "What Mechanisms Underlie Diastolic Dysfunction in Heart Failure?" *Cir. Res.* 94(12)1533-1542.

Kass, D.A. (Jan. 2009). "Rescuing a Failing Heart," *Nature Medicine* 15(11):24-25.

Katori, T. et al. (Mar. 3, 2004). "The Novel Organic Nitroxyl Donor, Isopropylamine/Nitric Oxide Exerts Beta-Independent Positive Inotropy/Lusitropy in Failing Hearts," Poster, *presented at American College of Cardiology*, New Orleans, LA, Mar. 9, 2004, *J. Am. Coll. Cardiol.* 43(5):218A, Abstract 1144-104.

Khan, S.S. et al. (Dec. 2008). "Managed Care Interventions for Improving Outcomes in Acute Heart Failure Syndromes," *The American Journal of Managed Care* 14(9):S273-S286.

Kim, W-K. et al. (Oct. 1999). "Attenuation of NMDA Receptor Activity and Neurotoxicity by Nitroxyl Anion, $NO^-$," *Neuron.* 24(2):461-469.

Kubalova, Z. et al. (Sep. 27, 2005; e-pub. Sep. 19, 2005). "Abnormal Intrastore Calcium Signaling in Chronic Heart Failure," *Proc. Natl. Acad. Sci. USA* 102(39):14104-14109.

Little, W.C. (Jun. 1985). "The Left Ventricular $dP/dt_{max}$-End-Diastolic Volume Relation in Closed-Chest Dogs," *Circ. Res.* 56(6):808-815.

Maclennan, D.H. et al. (Jul. 2003). "Phospholamban: A Crucial Regulator of Cardiac Contractility," *Nat. Rev. Mol. Cell Biol.* 4(7)566-577.

Mahaney, J.E. et al. (May 31, 2005, e-pub. May 5, 2005). "Intermolecular Conformational Coupling and Free Energy Exchange Enhance the Catalytic Efficiency of Cardiac Muscle SERCA2a following the Relief of Phospholamban Inhibition," *Biochemistry* 44(21):7713-7724.

Matter, C.M. et al. (May 11, 1999). "Effect of NO Donors on LV Diastolic Function in Patients With Severe Pressure-Overload Hypertrophy," *Circulation* 99(18):2396-2401.

Mongillo, M. et al. (Feb. 3, 2006; e-pub. Dec. 15, 2005). "Compartmentalized Phosphodiesterase-2 Activity Blunts β-Adrenergic Cardiac Inotropy via an NO/cGMP-Dependent Pathway," *Circ. Res.* 98(2):226-234.

Nieminen, M.S. et al. (2005). "Executive Summary of the Guidelines on the Diagnosis and Treatment of Acute Heart Failure," *European Heart Journal* 26:384-416.

Owan, T.E. et al. (Mar.-Apr. 2005). "Epidemiology of Diastolic Heart Failure," *Prog. Cardiovasc. Dis.* 47(5):320-332.

Paolocci, N. et al. (Jun. 2002). "The Cardiovascular Effects of HNO/Nitroxyl," *Nitric Oxide*, Abstract, 6(4):445.

Paulus, W.J. et al. (Oct. 2002). "Myocardial Contractile Effects of Nitric Oxide," *Heart Fail. Rev.* 7(4):371-383.

Petersen, J.W. et al. (2008). "Inotropes in the Management of Acute Heart Failure," *Crit. Care Med.* 36(1)(Suppl.):S106-S111.

Prestle, J. et al. (Jun. 2003). "$Ca^{2+}$-Handling Proteins and Heart Failure: Novel Molecular Targets?" *Curr. Med. Chem.* 10(11):967-981.

Quinones, M.A. (Mar.-Apr. 2005). "Assessment of Diastolic Function," *Prog. Cardiovasc. Dis.* 47(5):340-355.

Remme, W.J. et al. (2001). "Guidelines for the Diagnosis and Treatment of Chronic Heart Failure," *European Heart Journal* 22:1527-1560.

Schmidt, H.H.H.W. et al. (Dec. 10, 1996). "No NO from NO Synthase," *Proc. Natl. Acad. Sci. USA* 93(25):14492-14497.

Senzaki, H. et al. (Mar. 7, 2000). "Improved Mechanoenergetics and Cardiac Rest and Reserve Function of In Vivo Failing Heart by Calcium Sensitizer EMD-57033," *Circulation* 101(9):1040-1048.

Sham, J.S.K. et al. (Dec. 8, 1998). "Termination of $Ca^{2+}$Release by a Local Inactivation of Ryanodine Receptors in Cardiac Myocytes," *Proc. Natl. Acad. Sci. USA* 95(25):15096-15101. (Abstract Only).

Shin, D.D. et al. (Jan. 22, 2007). "Review of Current and Investigational Pharmacologic Agents for Acute Heart Failure of Syndromes," *Am. J. Cardiol.* 99(Suppl.):4A-23A.

Stoyanovsky, D. et al. (Jan. 1997). "Nitric Oxide Activates Skeletal and Cardiac Ryanodine Receptors," *Cell Calcium* 21(1):19-29. (Abstract Only).

Tocchetti, C.G. et al. (Jan. 5, 2007). "Nitroxyl Improves Cellular Heart Function by Directly Enhancing Cardiac Sarcoplasmic Reticulum $Ca^{2+}$Cycling," *Circulation Research* 100:96-104.

Written Opinion mailed on Nov. 17, 2006, for International Application No. PCT/US2006/024545, filed on Jun. 23, 2006, seven pages.

Xu, L. et al. (Jan. 9, 1998). "Activation of the Cardiac Calcium Release Channel (Ryanodine Receptor) by Poly-S-Nitrosylation," *Science* 279(5348):234-237.

Yturralde, F.R. et al. (Mar.-Apr. 2005). "Diagnostic Criteria for Diastolic Heart Failure," *Prog. Cardiovasc. Dis.* 47(5):314-319.

Zaccolo, M. et al. (Mar. 1, 2002). "Discrete Microdomains with High Concentration of cAMP in Stimulated Rat Neonatal Cardiac Myocytes," *Science* 295(5560):1711-1715.

Zahradníková, A. et al. (Dec. 1997). "Inactivation of the Cardiac Ryanodine Receptor Calcium Release Channel by Nitric Oxide," *Cell Calcium* 22(6):447-454.

Zhou, Y-Y. et al. (Dec. 1, 1999). "Constitutive $β_2$ -Adrenergic Signalling Enhances Sarcoplasmic Reticulum $Ca^{2+}$Cycling to Augment Contraction in Mouse Heart," *J. Physiol.* 52(Pt. 2):351-361.

Zile, M.R. et al. (Mar.-Apr. 2005). "Diastolic Heart Failure: Definitions and Terminology," *Prog. Cardiovasc. Dis.* 47(5):307-313.

Ziolo, M.T. et al. (Dec. 2001). "Positive and Negative Effects of Nitric Oxide on $Ca^{2+}$Sparks: Influence of β-Adrenergic Stimulation," *Am. J. Physiol. Heart Circ. Physiol.* 281(6):H2295-H2303.

Amendment with Request for Continued Examination mailed on Apr. 10, 2008, for U.S. Appl. No. 10/463,084, filed Jun. 16, 2003, 24 pages.

Non-Final Office Action mailed on Jul. 2, 2008, for U.S. Appl. No. 10/463,084, filed Jun. 16, 2003, 9 pages.

Bazylinski et al., "Metmyoglobin and Methemoglobin as Efficient Traps for Nitrosyl Hydride (Nitroxyl) in Neutral Aqueous Solution," *J. Am. Chem. Soc.* 107:7982-7986 (1985).

Bazylinski et al., "Evidence from the Reaction Between Trioxodinitrate (ii) and $^{15}NO$ That Trioxodinitrate (II) Decomposes into Nitrosyl Hydride and Nitrite in Neutral Aqueous Solution," *Inorg. Chem.* 24:4285-4288 (1985).

Bonner et al., "The Aqueous Solution Chemistry of Nitrogen in Low Positive Oxidation States," *Comments Inorg. Chem.* 7(4):215-2374 (1988).

Doyle et al., "Oxidation and Reduction of Hemoproteins by Trioxodinitrate (II). The Role of Nitrosyl Hydride and Nitrite," *J. Am. Chem. Soc.* 110:593-599 (1988).

King et al., "[22] Chemical Approaches Toward Generation of Nitroxyl," *Methods in Enzymology* 301:211-220 (1999).

Kohout et al., "On the Role of the Nitroxyl Molecule in the Reaction of Hydrogen Atoms with Nitric Oxide," *J. Ans. Chem. Soc.* 87(24):5795-5796 (1965).

Shafirovich et al., "Nitroxyl and its anion in aqueous solutions; Spin states, protic equilibria, and reactivities toward oxygen and nitric oxide," *Proc. Natl. Acad. Sci USA* 99(11):7340-7345 (2002).

Sharpe et al., "Reactions of Nitric oxide with mitochondrial cytochrom c: a novel mechanism for the formation of nitroxyl anion and peroxynitrite," *Biochem. J.* 332:9-19 (1998).

Smith et al., "The Alleged Role of Nitroxyl in Certain Reactions of Aldehydes and Alkyl Halides," *J. Am. Chem. Soc.*, 82:5731-5740 (1960).

\* cited by examiner

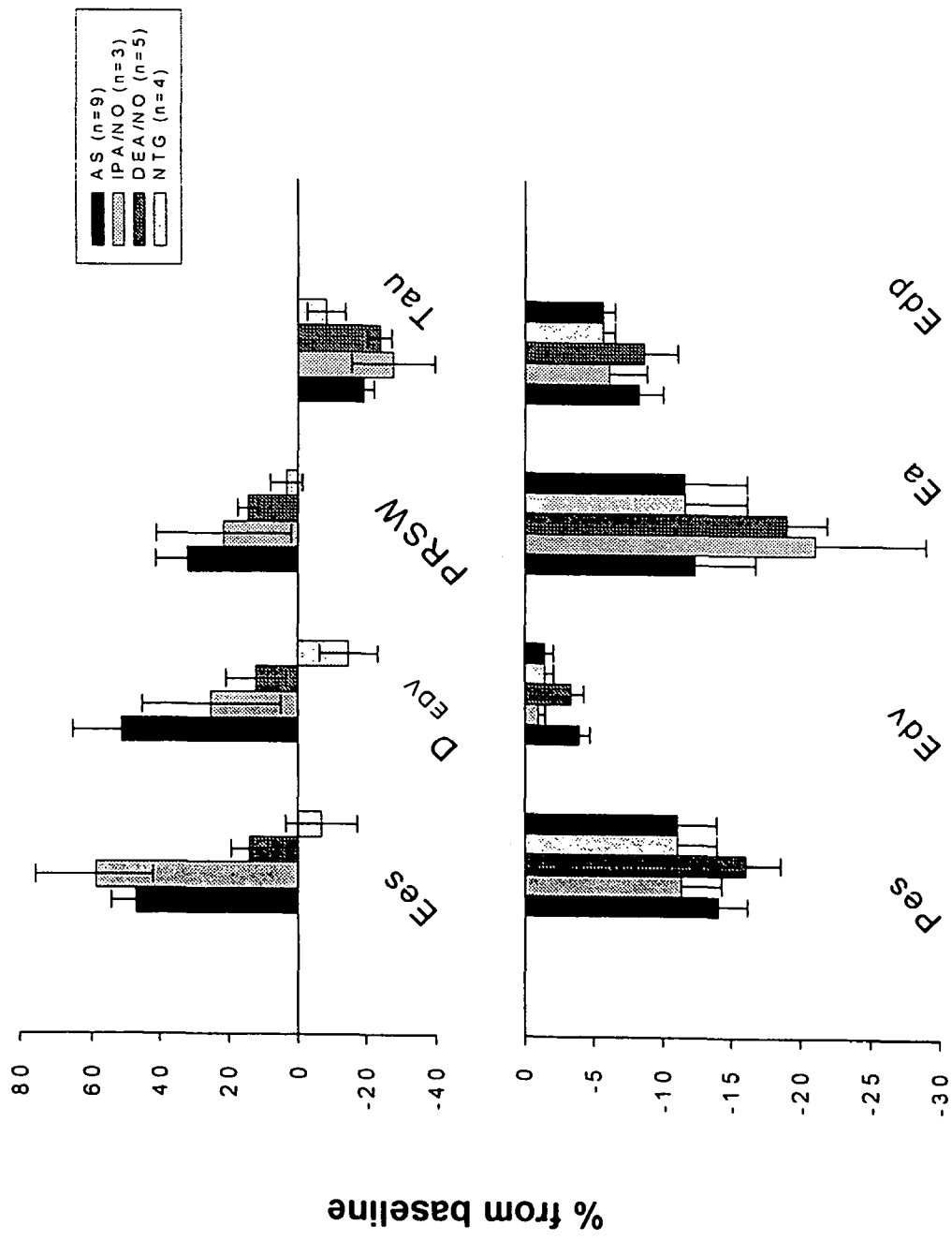
Fig. 1. Effects of Angeli's salt and IPA/NO (a novel nitroxyl donor) in CHF: a comparison with DEA/NO and NTG

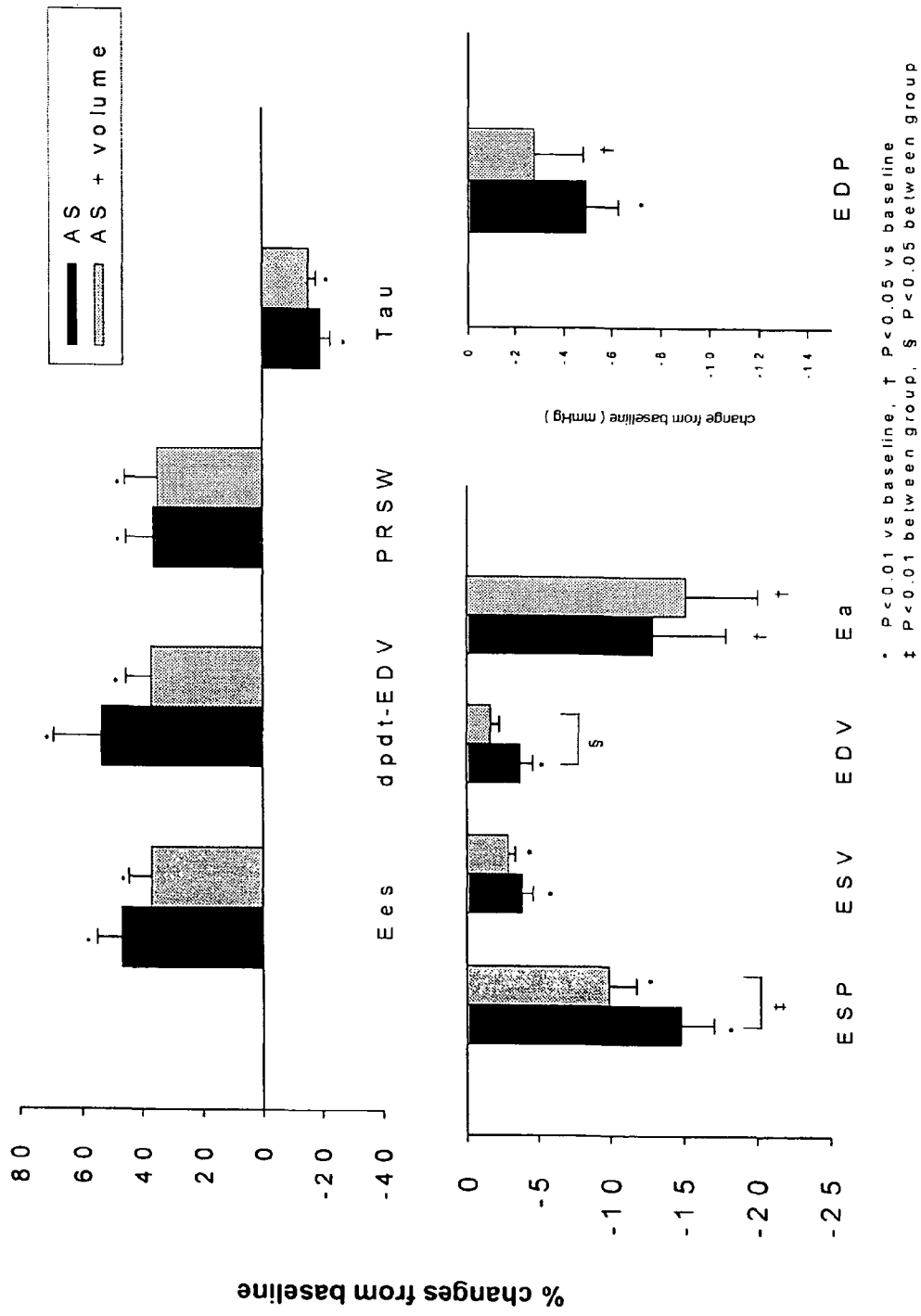

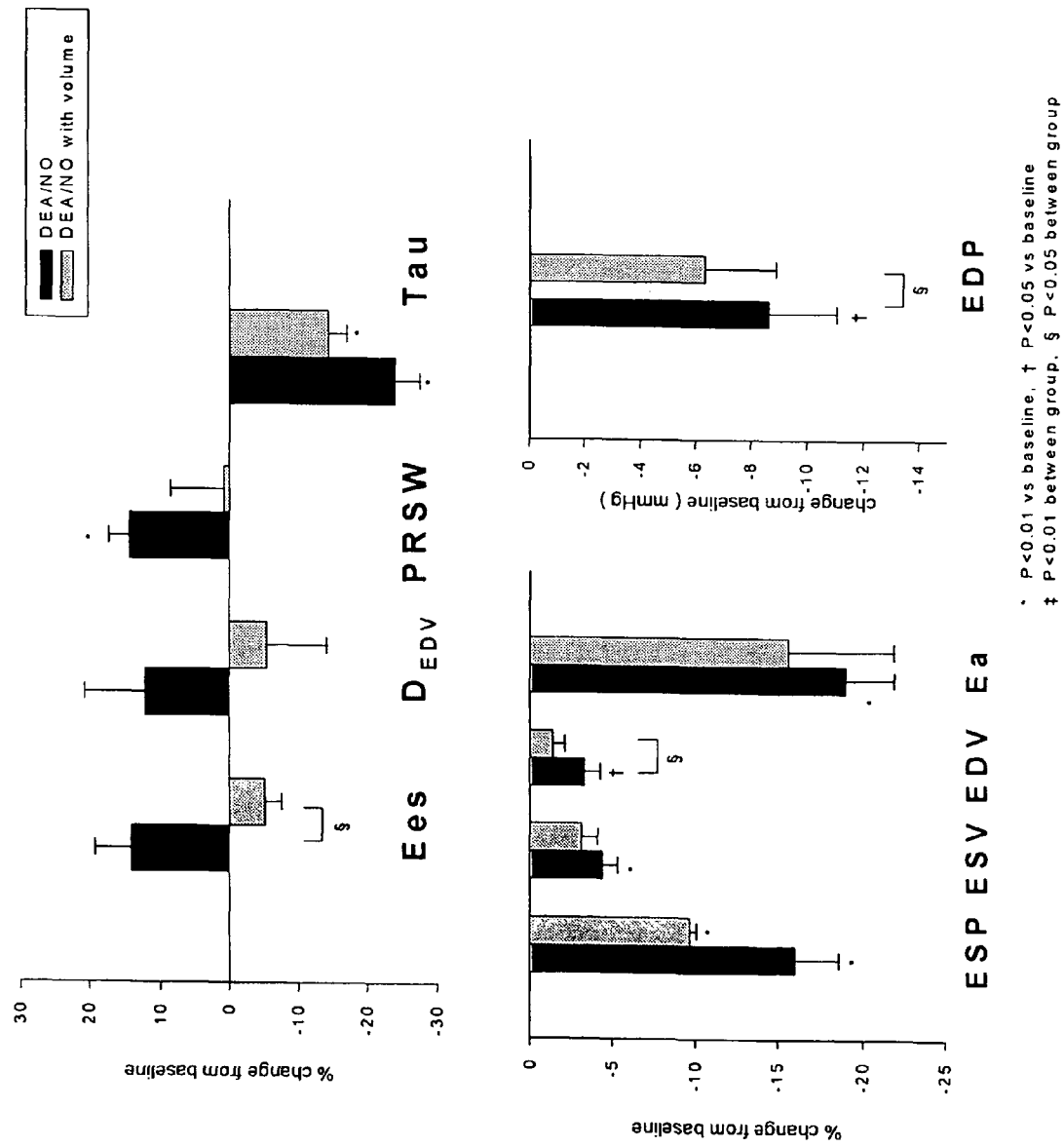

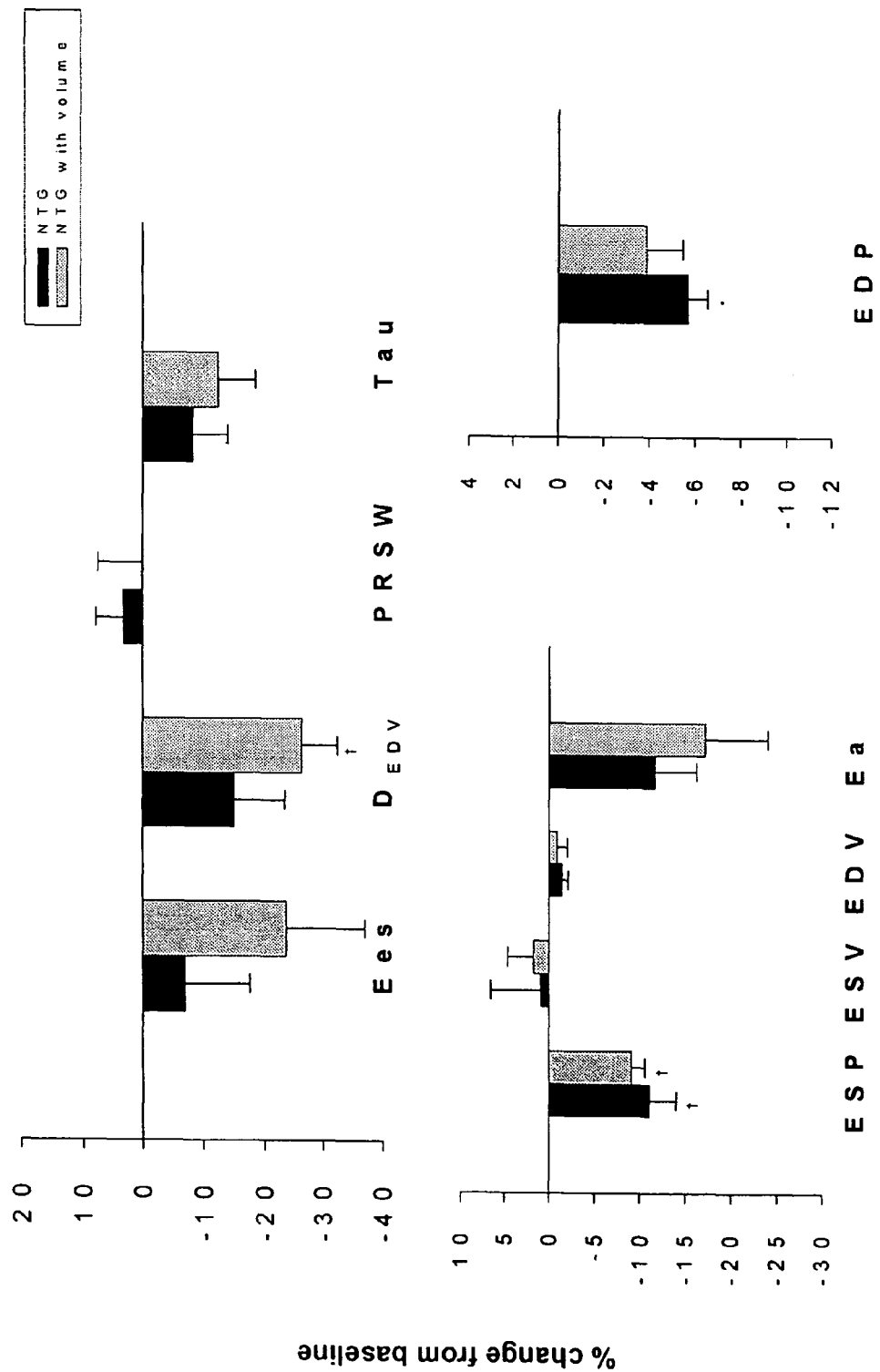

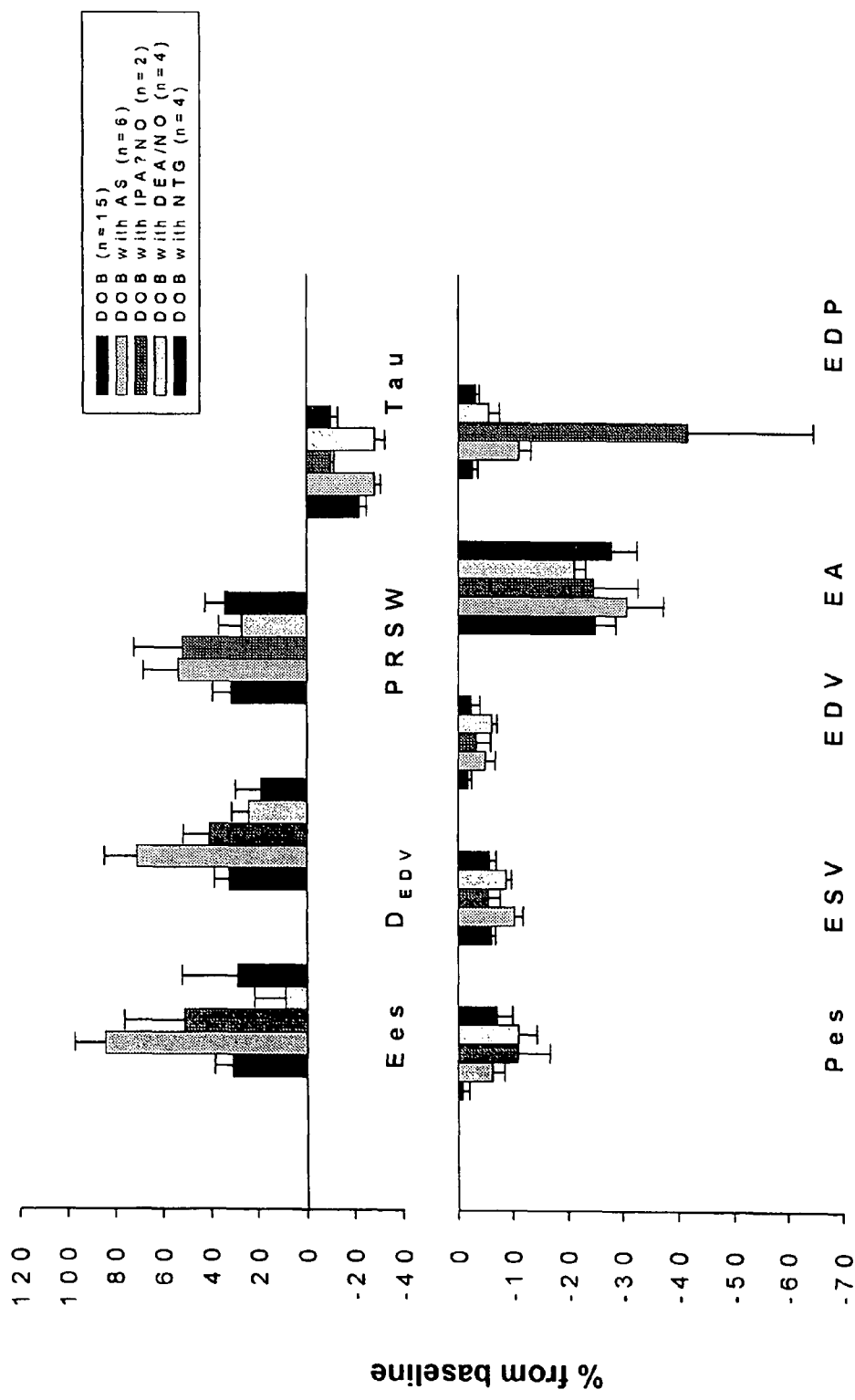

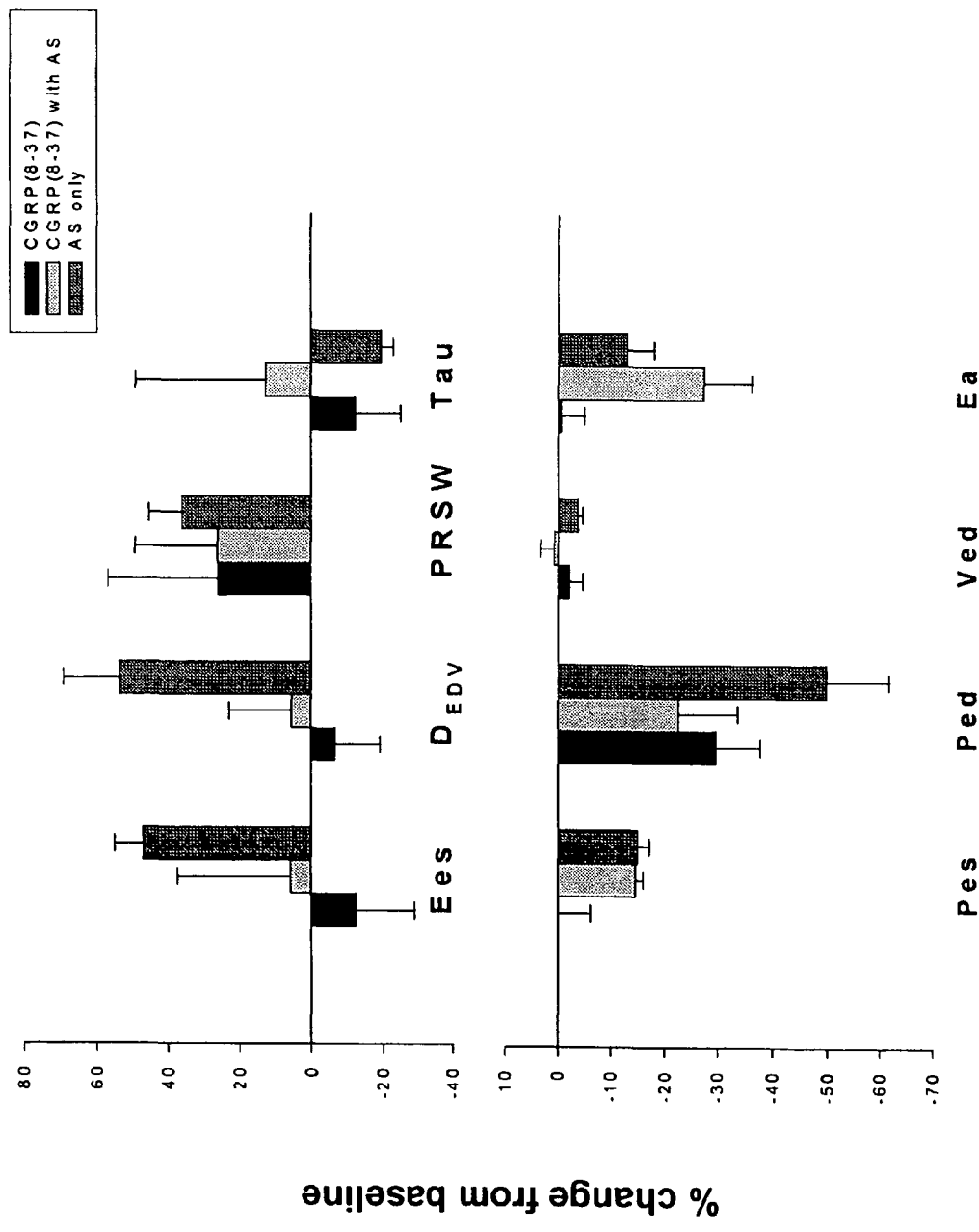

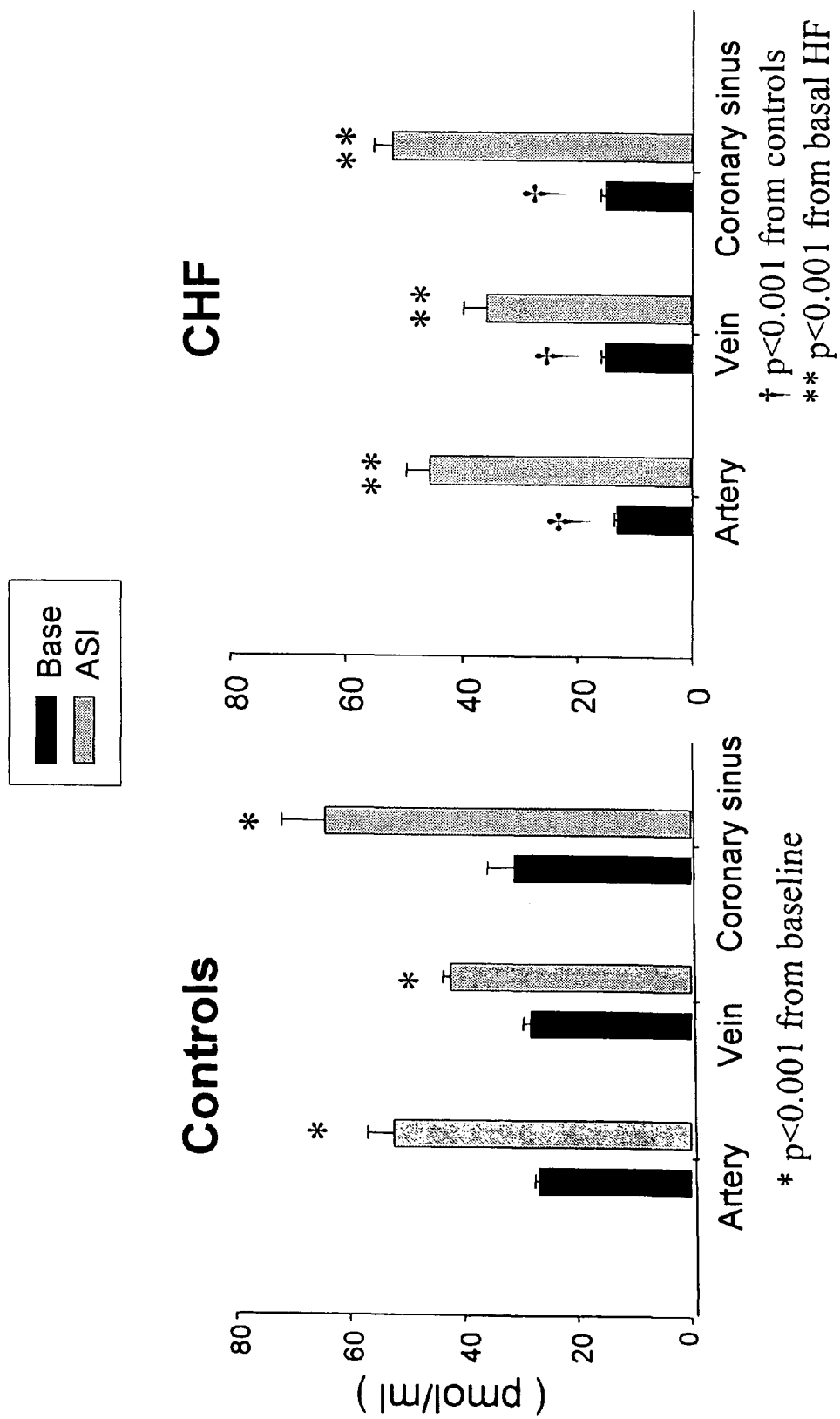
Fig. 7. CGRP levels in normal and CHF dogs, before and after stimulation with nitroxyl

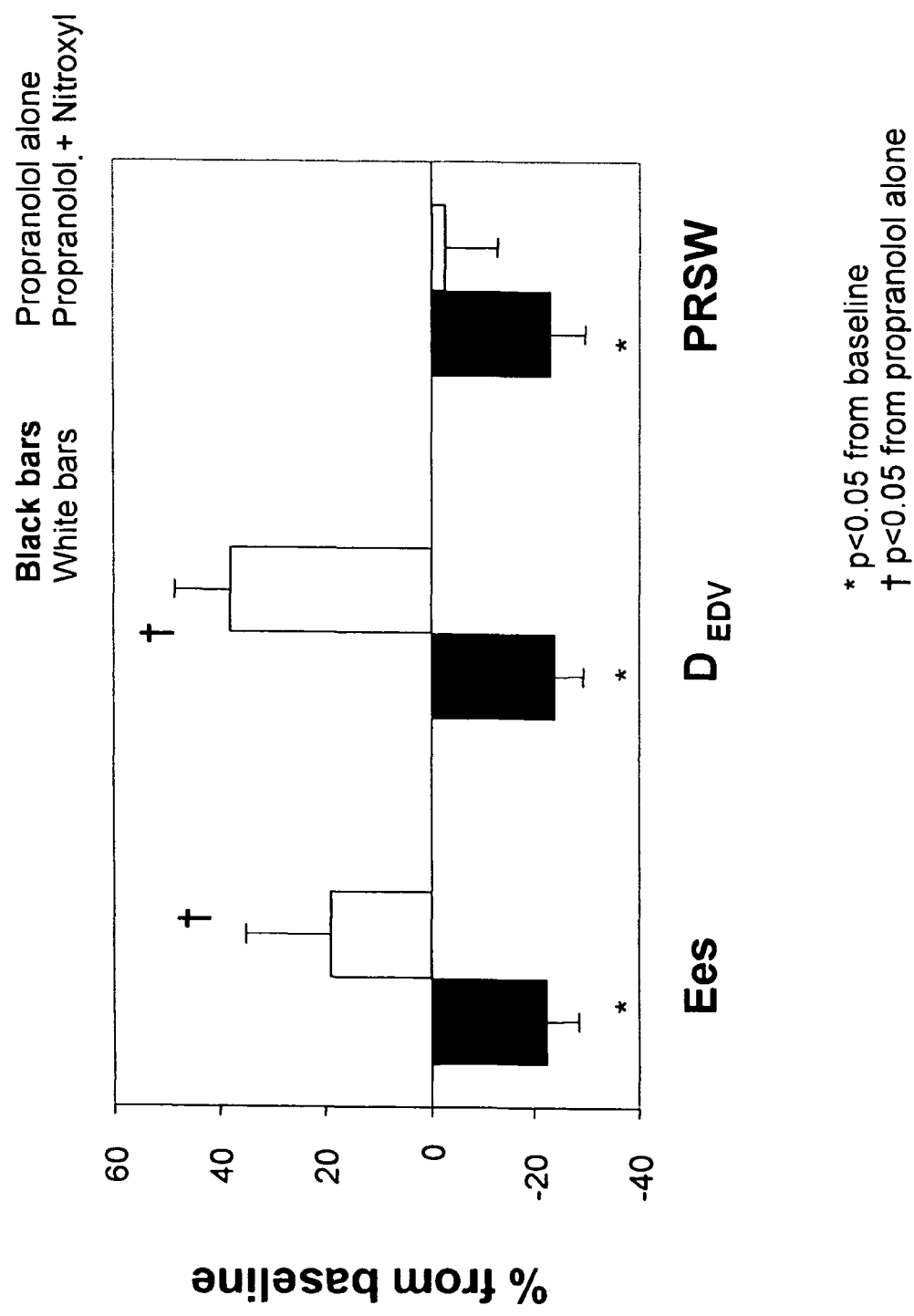
Fig. 8. Propranolol does not prevent nitroxyl-induced contractile effects (n=5)

NITROXYL PROGENITORS IN THE TREATMENT OF HEART FAILURE

This is a continuation application of application Ser. No. 10/226,412, filed Aug. 21, 2002, now U.S. Pat. No. 6,936,639.

FIELD

Pharmaceutical compounds and compositions are disclosed that are useful to treat heart failure.

BACKGROUND

Congestive heart failure (CHF) is a generally progressive, life threatening condition in which myocardial contractility is depressed such that the heart is unable to adequately pump the blood returning to it, also referred to as decompensation. Symptoms include breathlessness, fatigue, weakness, leg swelling, and exercise intolerance. On physical examination, patients with heart failure often have elevated heart and respiratory rates (an indication of fluid in the lungs), edema, jugular venous distension, and enlarged hearts. The most common cause of CHF is atherosclerosis, which causes blockages in the coronary arteries that provide blood flow to the heart muscle. Ultimately, such blockages may cause myocardial infarction with subsequent decline in heart function and resultant heart failure. Other causes of CHF include valvular heart disease, hypertension, viral infections of the heart, alcohol consumption, and diabetes. Some cases of CHF occur without clear etiology and are called idiopathic. The effects of CHF on a subject experiencing the condition can be fatal.

There are several types of CHF. Two types of CHF are identified according to which phase of the cardiac pumping cycle is more affected. Systolic heart failure occurs when the heart's ability to contract decreases. The heart cannot pump with enough force to push a sufficient amount of blood into the circulation leading to a reduced left ventricular ejection fraction. Lung congestion is a typical symptom of systolic heart failure. Diastolic heart failure refers to the heart's inability to relax between contractions and allow enough blood to enter the ventricles. Higher filling pressures are required to maintain cardiac output, but contractility as measured by left ventricular ejection fraction is typically normal. Swelling (edema) in the abdomen and legs is a typical symptom of diastolic heart failure.

CHF is also classified according to its severity. The New York Heart Association classification classifies CHF into four classes:

Class I—no obvious symptoms, with no limitations on physical activity;

Class II—some symptoms during or after normal activity, with mild physical activity limitations;

Class III—symptoms with less than ordinary activity, with moderate to significant physical activity limitations;

Class IV—significant symptoms at rest, with severe to total physical activity limitations.

Typically, a subject progresses through the classes as the subject lives with the condition.

Although CHF is generally thought of as a chronic, progressive condition, it can also develop suddenly. This type of CHF is called acute CHF, and it is a medical emergency. Acute CHF can be caused by acute myocardial injury that affects either myocardial performance, such as myocardial infarction, or valvular/chamber integrity, such as mitral regurgitation or ventricular septal rupture, which leads to an acute rise in left ventricular and diastolic pressure resulting in pulmonary edema, and dyspnea.

Common treatment agents for CHF include, vasodilators (drugs that dilate blood vessels), positive inotropes (drugs that increase the heart's ability to contract), and diuretics (drugs to reduce fluid). Additionally, beta-antagonists (drugs that antagonize beta-adrenergic receptors) have recently become standard agents for treating mild to moderate heart failure. Lowes et al., *Clin. Cardiol.*, 23:III11-6 (2000).

Positive inotropic agents include beta-adrenergic agonists, such as dopamine, dobutamine, dopexamine, and isoproterenol. Dobutamine is commonly given to subjects experiencing late-stage heart failure characterized by severely reduced ventricular ejection fraction or the inability of the subject to undertake physical activity without discomfort. Dobutamine is particularly effective for treating this type of heart failure because of its cardio-selectivity. U.S. Pat. No. 4,562,206 describes dobutamine's cardio-selectivity for the beta-1 adrenergic receptor relative to its activity at the vascular alpha and beta-2 adrenergic receptors. This cardio-selectivity results in a desired positive inotropic effect without a substantial, concomitant increase or decrease in blood pressure. Such blood pressure changes in subjects experiencing heart failure could cause further deterioration in heart function.

However, the use of beta-agonists has potential complications, such as arrhythmogenesis and increased oxygen demand by the heart. Additionally, the initial short-lived improvement of myocardial contractility afforded by these drugs is followed by an accelerated mortality rate resulting largely from a greater frequency of sudden death. Katz, HEART FAILURE: PATHOPHYSIOLOGY, MOLECULAR BIOLOGY AND CLINICAL MANAGEMENT, Lippincott, Williams & Wilkins (1999).

Beta-antagonists antagonize beta-adrenergic receptor function. While initially contra-indicated in heart failure, they have been found to provide a marked reduction in mortality and morbidity in clinical trials. Bouzamondo et al., *Fundam. Clin. Pharmacol.*, 15:95-109 (2001). Accordingly, they have become an established therapy for heart failure. Bouzamondo, supra. However, even subjects that improve under beta-antagonist therapy may subsequently decompensate and require acute treatment with a positive inotropic agent. Unfortunately, as their name suggests, beta-antagonists block the mechanism of action of the positive inotropic beta-agonists that are used in emergency care centers. Bristow et al., *J Card. Fail.*, 7:8-12 (2001).

Additionally, vasodilating agents are also used to treat heart failure. Vasodilators, such as nitroglycerin, have been used for a long period of time to treat heart failure. However, the cause of nitroglycerin's therapeutic effect was not known until late in the last century when it was discovered that the nitric oxide molecule (NO˙) was responsible for nitroglycerin's beneficial effects. In fact, the Nobel Prize was awarded in 1998 to three researchers who discovered NO˙'s beneficial effects. Opie & White in NITRATES IN DRUGS FOR THE HEART, W. B. Saunder, Philadelphia, 33-53 (2001), explain that such compounds are useful for treating heart failure due to their balanced venous and arterial vasorelaxant effects. U.S. Pat. No. 5,212,204 describes a group of NO˙ donating compounds containing the NONO group. The patent discloses that NO˙ donated from such compounds has vasodilative properties and can be useful to treat cardiac diseases that would respond favorably to a decrease in blood pressure, including acute congestive heart failure. The patent identifies Angeli's salt (sodium trioxodinitrate or $Na_2N_2O_3$) as such a compound. Angeli's salt is a compound that can decompose to donate either $NO^-$ or NO˙ depending on the oxidation state of the environment. Fitzhugh & Keefer, *Free Radical Biology & Medicine*, 28(10):1463-1469 (2000). For example, in the presence of oxidants such as ferricyanide, Angeli's salt decomposes to donate NO˙. Fitzhugh & Keefer, supra.

In some subjects experiencing heart failure, a nitric oxide donor is administered in combination with a positive inotropic agent to both cause vasodilation and to increase myocardial contractility. However, this combined administration can impair the effectiveness of positive inotropic treatment agents. For example, Hart et al., *Am. J. Physiol. Heart Circ. Pyhsiol.*, 281:146-54 (2001) reported that administration of the nitric oxide donor sodium nitroprusside, in combination with the positive inotropic, beta-adrenergic agonist dobutamine, impaired the positive intotropic effect of dobutamine. Hare et al., *Circulation*, 92:2198-203 (1995) also disclosed the inhibitory effect of NO˙ on the effectiveness of dobutamine.

Researchers have also investigated other forms of nitric oxide to determine their effects on the heart. The nitroxyl species includes the nitroxyl anion ($NO^-$), which is the one-electron reduction product of NO˙. Depending on the pH of the environment, the nitroxyl anion may be protenated to HNO. Experiments testing the effects of $NO^-$ donors in cardiac diseases have demonstrated that $NO^-$ can have a deleterious effect on the myocardium when given to reperfused myocardium. In fact, Ma et al., *Proc. Nat'l Acad. Sci.*, 96(25): 14617-14622 (1999) reported that administration of Angeli's salt as an $NO^-$ donor to anesthetized rabbits 5 minutes prior to reperfusion (after ischemia) increased myocardial ischemia/reperfusion injury. Also, Takahira et al., *Free Radical Biology & Medicine*, 31(6):809-815 (2001) reported that administration of Angeli's salt as an $NO^-$ donor during ischemia and 5 minutes before reperfusion of rat renal tissue contributed to neutrophil infiltration into the tissue, which is believed to cause ischemia/reperfusion injury.

Patent Cooperation Treaty (PCT) international application PCT/US00/12957 discloses administering a charged nitric oxide species to offset the adverse effects of a potassium channel activator in a method of administering a potassium channel activator to prevent or treat cardiovascular disorders including, among others, congestive heart failure. The only $NO^-$ donors described in the application are thionitrates that form disulfide species.

SUMMARY

The inventors discovered that administration of a nitroxyl ($HNO/NO^-$) donating compound, such as Angeli's salt, increased myocardial contractility while it concomitantly lowered left ventricular preload in subjects experiencing heart failure. Moreover, administration of the $HNO/NO^-$ donating compound isopropylamine $(IPA)/NO(Na(CH_3)_2CHNHN(O)NO)$ surprisingly exhibited positive inotropic effects in subjects experiencing heart failure that were superior to those caused by the $HNO/NO^-$ donating compound Angeli's salt. Additionally, in contrast to the effects observed with NO˙ donors, administration of an $HNO/NO^-$ donor in combination with a positive inotropic agent did not impair the positive inotropic effect of the positive inotropic agent. Further, the inventors discovered that $HNO/NO^-$ exerts its positive inotropic effect independent of the adrenergic system, increasing contractility even in subjects receiving beta-antagonist therapy.

Accordingly, due to their concomitant positive inotropic/lusotropic action and unloading effects, $HNO/NO^-$ donors are helpful in treating cardiovascular diseases characterized by high resistive load and poor contractile performance. In particular, $HNO/NO^-$ donating compounds such as IPA/NO are useful treatment agents for heart failure. Moreover, these agents are useful when used in combination with other positive inotropic agents, such as beta-adrenergic agonists for example, dobutamine. Additionally, $HNO/NO^-$ donors are useful for treating heart failure in subjects receiving beta-antagonist therapy.

Provided herein are methods of treating heart failure by administering a therapeutically effective dose at least one $HNO/NO^-$ donating compound to a subject experiencing heart failure. Also provided are methods of administering a therapeutically effective dose of at least one $HNO/NO^-$ donating compound in combination with at least one other positive inotropic agent to a subject experiencing heart failure. Further provided are methods of administering a therapeutically effective dose of at least one $HNO/NO^-$ donating compound to a subject who is receiving beta-antagonist therapy and who is experiencing heart failure.

More particularly, methods are provided herein for administering compounds containing the N-oxy-N-nitroso group (diazeniumdolates), which donate $HNO/NO^-$, to treat heart failure. Such compounds include Angeli's salt, IPA/NO, and analogs and derivatives of such compounds. Additionally, methods are provided herein for administering such compounds in combination with beta-adrenergic agonists to treat heart failure. Such agonists include dopamine, dobutamine, and isoproterenol, and analogs and derivatives of such compounds. Also provided are methods of administering $HNO/NO^-$ donors to subjects receiving treatment with beta-antagonizing agents such as propranolol, metoprolol, bisoprolol, bucindolol, and carvedilol. Further, methods are provided herein for treating specific classifications of heart failure, such as Class III heart failure and acute heart failure.

These and other features and aspects of the disclosed methods will become more apparent and better understood with regard to the following figures and description.

BRIEF DESCRIPTION OF THE FIGURES

FIG. 1 shows the percentage change from a baseline for several diagnostic tests of hearts of conscious dogs experiencing congestive heart failure (CHF) resulting from administration of the $HNO/NO^-$ donating compounds Angeli's salt (AS) and isoproylamine/NO (IPA/NO), as well as the NO˙ donors diethylamine/NO (DEA/NO) and nitroglycerin (NTG). The diagnostic tests included end-systolic elastance (Ees), preload-normalized maximal change in pressure over change in time dP/dt ($D_{EDV}$), pre-load recruitable stroke work (PRSW), the time constant of ventricular relaxation (tau), end systolic pressure (Pes), end diastolic volume (Edv), arterial resistance (Ea), and end diastolic pressure (Edp).

FIG. 2 shows the percentage change from a baseline for several diagnostic tests of hearts of conscious dogs experiencing CHF resulting from the administration of the $HNO/NO^-$ donating compound Angeli's salt (AS), and the administration of AS when the dog hearts were under loading conditions (AS+volume). The diagnostic tests included Ees, preload-normalized maximal change in pressure over change in time dP/dt (dPdt-EDV), PRSW, tau, end systolic pressure (ESP), end systolic volume (ESV), end diastolic volume (EDV), Ea, and end diastolic pressure (EDP).

FIG. 3 shows the percentage change from a baseline for several diagnostic tests of hearts of conscious dogs experiencing CHF resulting from the administration of the NO˙ donating compound DEA/NO and the administration of DEA/NO when the dog hearts were under a load (DEA/NO with volume). The diagnostic tests included Ees, $D_{EDV}$, PRSW, tau, ESP, ESV, EDV, Ea, and EDP.

FIG. 4 shows the percentage change from a baseline for several diagnostic tests of hearts of conscious dogs experiencing CHF resulting from the administration of the NO⁻ donating compound nitroglycerin (NTG) and the administration of NTG when the dog hearts were under a load (volume loading). The diagnostic tests included Ees, $D_{EDV}$, PRSW, tau, ESP, ESV, EDV, Ea, and EDP.

FIG. 5 shows the percentage change from a baseline for several diagnostic tests of hearts of conscious dogs experiencing CHF resulting from the administration of the positive inotropic agent dobutamine (DOB) in combination with the HNO/NO⁻ donating compounds AS and IPA/NO and the NO⁻ donating compounds DEA/NO and NTG. The diagnostic tests included Ees, $D_{EDV}$, PRSW, tau, Pes, ESV, EDV, arterial resistance (EA), and EDP.

FIG. 6 shows the percentage change from a baseline for several diagnostic tests of hearts of conscious dogs experiencing heart failure (HF) resulting from the administration of calcitonin gene-related peptide$_{8-37}$ (CGRP$_{8-37}$), administration of CGRP$_{8-37}$ in combination with AS, and administration of AS alone. The diagnostic tests included Ees, $D_{EDV}$, PRSW, tau, Pes, end diastolic pressure (Ped), end diastolic volume (Ved), and Ea.

FIG. 7 shows the blood plasma CGRP levels in picomoles (pmol) per milliliter (ml) in the artery, vein, and coronary sinus of normal conscious dogs (controls) and conscious dogs experiencing heart failure.

FIG. 8 shows the percentage change from a baseline for several diagnostic tests of hearts of normal conscious dogs, which dogs were under beta-antagonist therapy with propranolol, resulting from administration of the HNO/NO⁻ donating compound AS. The tests included Ees, $D_{EDV}$, and PRSW.

DETAILED DESCRIPTION

Disclosed herein is a method of treating CHF by administering a therapeutically effective dose of at least one nitroxyl (HNO/NO⁻) donating compound to a subject experiencing heart failure. In particular embodiments the HNO/NO⁻ donating compound is IPA/NO. In other particular embodiments the HNO/NO⁻ donating compound is Piloty's acid. Also disclosed herein is a method of treating CHF by administering a therapeutically effective dose of at least one HNO/NO⁻ donating compound in combination with a therapeutically effective dose of at least one positive inotropic agent to a subject experiencing heart failure. In particular embodiments the HNO/NO⁻ donating compound is a diazeniumdolate, such as IPA/NO, and the positive inotrope is a beta-adrenergic agonist, such as dobutamine. Additionally, in particular embodiments of the methods described above, the HNO/NO⁻ donating compound or the combination of the HNO/NO⁻ donating compound and the positive inotropic compound are used to treat Class III CHF, or other non-acute CHF. In still other embodiments the methods are used to treat acute CHF. Also disclosed is a method of treating CHF in a subject receiving beta-antagonist therapy by administering a therapeutically effective dose of at least one HNO/NO⁻ donating compound. In particular embodiments the HNO/NO⁻ donating compound is a diazeniumdolate, such as Angeli's salt.

A nitroxyl donor is an agent or compound that provides a physiologically effective amount of HNO or NO⁻ (HNO/NO⁻). The HNO/NO⁻ donating compound is any compound that donates HNO/NO⁻ and has a safety profile indicating the compound would be tolerated by a subject in the amount necessary to achieve a therapeutic effect. One of ordinary skill in the art would be able to determine the safety of administering particular compounds and dosages to live subjects. Such a compound includes any compound having the formula

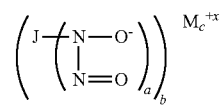

wherein J is an organic or inorganic moiety, $M^{+x}$ is a pharmaceutically acceptable cation, wherein x is the valence of the cation, a is 1 or 2, b and c are the smallest integers that result in a neutral compound, and wherein the compound is administered under conditions that cause it to release HNO/NO⁻. The compounds of Formula I are known generally as diazeniumdolates because they contain the N-oxy-N-nitroso complex. Angeli's salt is a compound of formula I that disassociates under physiological conditions to donate HNO/NO⁻. Other diazeniumdolates that disassociate under physiological conditions to generate HNO/NO⁻, such as IPA/NO or Sulfi/NO (N-nitrosohydroxylamine-N-sulfonate/ammonium salt), are also used in performing the method. Additionally, analogs and derivatives of such compounds can be used. Moreover, conditions, such as the oxidation state of the environment, can be altered to cause such compounds to donate HNO/NO⁻.

An analog is a molecule that differs in chemical structure from a parent compound, for example a homolog (differing by an increment in the chemical structure, such as a difference in the length of an alykl chain), a molecular fragment, a structure that differs by one or more functional groups, or a change in ionization. Structural analogs are often found using quantitative structure activity relationships (QSAR), with technologies such as those disclosed in Remington: *The Science and Practice of Pharmacology*, 19$^{th}$ Edition (1995), chapter 28. A derivative is a biologically active molecule derived from the base structure.

Wang et al., "New chemical and biological aspects of S-nitrosothiols," *Curr. Med. Chem.*, 7(8):821-34 (2000), describes NO⁻ formation from heterolytic decomposition of S-nitrosothiol compounds. Thus, S-nitrosothiol compounds such as S-nitroso-L-cystine ethyl ester, S-nitroso-L-cystine, S-nitroso-glutathione, S-nitroso-N-acetyl-cystine, S-nitroso-3-mercaptoetanol, S-nitroso-3-mercaptopropanoic acid, S-nitroso-2-aimonethanethiol, S-nitroso-N-acetyl penicillamine (SNAP), S-nitrosocaptopril, as well as others are also used in performing the provided method. In particular, S-nitrosoglutathione (GNSO) has been reported as capable of being reduced to HNO/NO⁻ in the presence of thiols. Hogg et al., *Biochem. J*, 323:477-481 (1997).

Piloty's acid (benzenesulfohydroxamic acid) is a hydroxamic acid (X(=O)NHOH) that donates HNO/NO⁻ and is useful in performing the provided methods. Other hydroxamic acids that donate HNO/NO⁻, in particular, other sulfohyrdoxamic acids and their derivatives are also useful.

Thionitrates (R—(S)—NO$_2$, wherein R is a polypeptide, an amino acid, a sugar, a modified or unmodified oligonucleotide, a straight or branched, saturated or unsaturated, aliphatic or aromatic, substituted or unsubstituted hydrocarbon, or a heterocylclic group) that donate HNO/NO⁻ are useful in performing the methods provided. In particular, such compounds that form disulfide species are useful.

One of ordinary skill in the art would be able to determine these and other compounds capable of donating HNO/NO⁻. Also included in this term is direct administration of HNO/NO⁻.

Compositions comprising more than one HNO/NO⁻ donating compound are also used. For example, IPA/NO and another compound that dissociates to generate HNO/NO⁻ for example, Piloty's acid, are used to treat heart failure.

In particular embodiments the HNO/NO⁻ donating compound is administered in the form of a pharmaceutical composition. A pharmaceutical composition comprising an effective amount of the HNO/NO⁻ donating compound as an active ingredient could be easily prepared by standard procedures well known in the art, with pharmaceutically acceptable non-toxic solvents and/or sterile carriers, if necessary. Such preparations are administered orally or in injectable form, or directly to myocardial tissue. In other embodiments the HNO/NO⁻ donor is administered without a pharmaceutical carrier. In particular embodiments the HNO/NO⁻ donor is administered by a short-term infusion, such as for 5 to 20 minutes. In other embodiments the HNO/NO⁻ donor is administered by a long-term infusion, such as from 3-4 hours. The HNO/NO⁻ donated by Angeli's salt retains its beneficial effects during 3-4 hours of perfusion.

The dose of the HNO/NO⁻ donating compound is a therapeutically effective dose. A therapeutically effective dose of an HNO/NO⁻ donating compound comprises a dose effective to increase contractility in a subject experiencing heart failure. Optimizing therapy to be effective across a broad population can be performed with a careful understanding of various factors to determine the appropriate therapeutic dose, in view of the inventors' disclosure that these agents cause a positive inotropic effect as well as venous dilation. In particular embodiments, an infusion of 10 micrograms (μg)/kilogram of body weight (kg)/minute (min) is administered for 5-20 min to treat acute heart failure. In one example, the agent administered at this dose is Angeli's salt. In other embodiments an infusion of 2.5 μg/kg/min is administered for 5-20 min to treat acute heart failure. In one example, the agent administered at this dose is IPA/NO.

A positive inotrope is an agent or compound that causes an increase in myocardial contractile function. Such an agent includes a beta-adrenergic receptor agonist, an inhibitor of phophodiesterase activity, and calcium-sensitizers. Beta-adrenergic receptor agonists include, among others, dopamine, dobutamine, terbutaline, and isoproterenol. Analogs and derivatives of such compounds are also used. For example, U.S. Pat. No. 4,663,351 describes a dobutamine prodrug that can be administered orally. One of ordinary skill in the art would be able to determine these and other compounds that are capable of causing positive inotropic effects and also additional beta-agonist compounds. In particular embodiments the beta-receptor agonist is selective for the beta-1 receptor. However, in other embodiments the beta-agonist is selective for the beta-2 receptor, or is not selective for any particular receptor. Additionally, compositions comprising more than one positive inotropic agent are used. For example, dobutamine and isoproterenol are used to treat heart failure.

In particular embodiments the positive inotropic agent is administered in combination with the HNO/NO⁻ donor. The combined administration of the HNO/NO⁻ donor and the positive inotropic agent comprises administering the HNO/NO⁻ donor either sequentially with the positive inotropic agent for example, the treatment with one agent first and then the second agent, or administering both agents at substantially the same time, wherein there is an overlap in performing the administration. With sequential administration a subject is exposed to the agents at different times, so long as some amount of the first agent, which is sufficient to be therapeutically effective in combination with the second agent, remains in the subject when the other agent is administered. Treatment with both agents at the same time can be in the same dose, such as a physically mixed dose, or in separate doses administered at the same time.

In particular embodiments the positive inotropic agent is administered in the form of a pharmaceutical composition. A pharmaceutical composition comprising an effective amount of the positive inotropic agent as an active ingredient could be easily prepared by standard procedures well known in the art, with pharmaceutically acceptable non-toxic solvents and/or sterile carriers, if necessary. Such preparations are administered orally or in injectable form, or directly to myocardial tissue. In other embodiments the positive inotropic agent is administered without a pharmaceutical carrier.

The dose of the positive inotropic agent is a therapeutically effective dose. In particular embodiments positive inotropic agent is administered at a dose of between 2 and 20 μg/kg/min. In certain examples dobutamine is administered at this dose. However, in other embodiments, higher and lower dosages are administered to subjects experiencing heart failure. For example, a dose of 0.5 μg/kg/min is administered, or a dose of 40 μg/kg/min is administered. Optimizing therapy to be effective across a broad population can be performed with a careful understanding of various factors to determine the appropriate therapeutic dose, in view of the inventors' disclosure that the positive inotropic agent is administered in combination with an HNO/NO⁻ donor.

In particular embodiments an HNO/NO⁻ donor is administered to a subject experiencing heart failure that is receiving beta-antagonist therapy. A beta-antagonist (also known as a beta-blocker) includes any compound that effectively acts as an antagonist at a subject's beta-adrenergic receptors, and provides desired therapeutic or pharmaceutical results, such as diminished vascular tone and/or heart rate. In particular embodiments the beta-antagonist is selective for a particular receptor, such as the beta-1 receptor. In other embodiments the beta-antagonist is not selective for any particular beta receptor. Beta-antagonizing agents include metoprolol, bisoprolol, bucindolol, carvedilol, timolol, propranolol, pindolol, and atenolol. One of ordinary skill in the art would be able to identify these and other compounds that are capable of acting as beta-adrenergic antagonists at a subject's beta-adrenergic receptors.

A subject who is receiving beta-antagonist therapy is any subject to whom a beta-antagonist has been administered, and in whom the beta-antagonist continues to act as an antagonist at the subject's beta-adrenergic receptors. In particular embodiments a determination of whether a subject is receiving beta-blocking therapy is made by examination of the subject's medical history. In other embodiments the subject is screened for the presence of beta-blocking agents by chemical tests, such as high-speed liquid chromatography as described in Thevis et al., *Biomed. Chromatogr.*, 15:393-402 (2001).

The administration of an HNO/NO⁻ donating compound either alone, in combination with a positive inotropic agent, or to a subject receiving beta-antagonist therapy, is used to treat heart failure of all classifications. In particular embodiments an HNO/NO⁻ donating compound is used to treat early-stage chronic heart failure, such as Class II heart failure. In other embodiments an HNO/NO⁻ donating compound is used in combination with a positive inotropic agent, such as isoproterenol to treat Class IV heart failure. In still other embodiments an HNO/NO⁻ donating compound is used in combination with a positive inotropic agent, such as isoproterenol to treat acute heart failure. In some embodiments, when HNO/NO⁻ is used to treat early stage heart failure, the dose administered is lower than that used to treat acute heart failure. In other embodiments the dose is the same as is used to treat acute heart failure.

The following are non-limiting examples of particular embodiments of the methods provided herein.

EXAMPLE 1

This example demonstrates that infusion of an HNO/NO⁻ donor caused positive inotropic effects in failing myocardium. Further, infusion of an HNO/NO⁻ donor complemented the positive inotropic effect of dobutamine, as opposed to the impairment of dobutamine's positive inotropic effect observed with NO· donors. Additionally, when compared with an infusion of Angeli's salt designed to cause a systemic blood pressure decrease nearly equivalent to that caused by IPA/NO, the HNO/NO⁻ donor IPA/NO exerted a stronger positive inotropic effect.

The effect of HNO/NO⁻ donated by AS (10 micrograms (μg)/kilogram (kg)/minute (min) for 5-20 min) and IPA/NO (2.5-5.0 μg/kg/min for 5-20 min) on basal cardiovascular function was tested in mongrel dogs. Studies were performed at a constant heart rate during atrial pacing (130-160 beats per minute). Myocardial effects produced by HNO/NO⁻ donating compounds were compared to those produced by the NO· donors DEA/NO and nitroglycerin at doses titrated to achieve the same decline in systolic pressure (a measure of systemic blood pressure) as the HNO/NO⁻ donors.

Hemodynamic data was sampled at 250 Hertz (Hz) and steady-state and pressure-dimension parameters were derived. Since in vivo cardiac contractility assessment requires separation of the effects of chamber loading, pressure-volume relation indexes, specifically, the end-systolic elastance (Ees), and the slope of $dP/dt_{max}$-end-diastolic dimension ($D_{EDV}$) relations were employed. Isovolumic relaxation was derived from pressure decay waveforms assuming a nonzero decay asymptote.

Serum concentrations of nitrite and nitrate were determined by a modified Griess assay, with and without prior chemical reduction of nitrate to nitrite using $VCl_3$. Serum stored at −70° C. was deproteinized by ultrafiltration (30 kilodalton (kD) cut-off, Centricon, Sartorius) at 4° C., and absorbance at 540 nanometer (nm) read using a plate reader (Perkin Elmer HTS 7000 BioAssay Reader controlled by TECAN WinSelect software) after a 37° C. incubation with Griess reagents for 30-45 min.

With reference to FIG. 1, each compound tested was administered in doses titrated to achieve nearly equivalent end systolic pressures (Pes) in order to allow comparison between equivalent levels of dilation. Angeli's salt and IPA/NO caused significant increases in contractility during heart failure as measured by Ees, $D_{EDV}$, and PRSW. These increases were much greater than the small increases observed with DEA/NO and were opposite of the negative inotropic effects observed with nitroglycerin. Additionally, both Angeli's salt and IPA/NO reduced the cardiac load as measured by Edv (preload) and Ea (afterload). Surprisingly, IPA/NO caused a greater increase in cardiac contractility than Angeli's salt as measured by Ees, which, being load-independent, is a good parameter for assessing myocardial contractility. This is especially surprising because the doses of IPA/NO were one-half to one-quarter the doses of Angeli's salt.

With reference to FIG. 2, the administration of HNO/NO⁻ exhibited a positive inotropic effect, which was not dependent on cardiac load. As illustrated by the measurements of Ees and PRSW for both loaded and unloaded states, HNO/NO⁻ exerted a nearly equivalent positive inotropic effect regardless of cardiac load. This indicates that the contractility increases caused by HNO/NO⁻ are primary as opposed to secondary effects. In contrast, with reference to FIG. 3, the minor positive inotropic effects observed with the administration of NO· (DEA/NO) were reversed when the heart was under cardiac load conditions, that is at matched end-diastolic volume. Moreover, FIG. 4 illustrates that administration of the NO· donor nitroglycerin caused contractility to decrease when administered alone, and caused an even greater negative inotropic effect under loading conditions. This indicates that the minor contractility increase observed with DEA/NO is merely secondary to the vasodilatory effects of the compound. That is, NO· has no direct positive inotropic effects because any increases in contractility were abolished upon volume repletion.

With reference to FIG. 5, administration of AS and IPA/NO resulted in a greater positive inotropic effect than administration of dobutamine alone. For example, administration of AS resulted in a more than doubling of Ees over administration of dobutamine alone. In contrast, administration of DEA/NO and nitroglycerin reduced the positive inotropic effect of dobutamine, as illustrated by the decrease in Ees when the dobutamine was administered with DEA/NO and NTG.

EXAMPLE 2

This example demonstrates that the positive inotropic effect of HNO/NO⁻ is a function of its stimulation of calcitonin gene-related peptide (CGRP) signaling rather than a function of beta-agonism.

To test the relation between the inotropic action of HNO/NO⁻ and calcitonin gene-related peptide (CGRP) signaling, CGRP receptors in mongrel dogs were antagonized using the selective antagonist $CGRP_{8-37}$ (400 μg in 30 milliliters (ml) of saline bolus, then 2.6 μg/kg/min for 15 min). Plasma CGRP levels measurements were performed by sampling the blood of the dogs. Blood samples (2.5 ml) were withdrawn from arterial, venous, and coronary sinus catheters. After sampling, catheters were flushed with heparanized saline. Samples were centrifuged at 1600 times gravity (g) for 20 minutes at 4° Celcius (C). Plasma was then separated and stored at −20° C. until analysis. Plasma (0.5 ml) was used to extract CGRP by addition of 0.8 ml of ethanol. The mixture was centrifuged at 1600 g for 20 minutes. After removing the supernatant, the extracted samples were air dried at room temperature overnight and then stored at 4° C. Immediately prior to assay, dried samples were reconstituted with assay buffer following manufacturer's instructions (Peninsula Labs) and assayed for CGRP by radioimmunoassay (RIA). CGRP antiserum, code RAS 6012, was used. The dynamic assay range was 1-128 picograms (pg) per 300 microliters (μL) of sample. Stimulation with HNO/NO⁻ donors and diagnostic tests were performed as described above in Example 1.

With reference to FIG. 6, administration of the selective CGRP antagonist $CGRP_{8-37}$ resulted in a modest negative inotropic effect during heart failure as measured by Ees. This result was not unexpected given that CGRP is known positive inotrope. Doggrell, *Expert Opin. Investig. Drugs,* 10:1131-8 (2001). More interestingly, $CGRP_{8-37}$ effectively prevented the HNO/NO⁻-mediated, positive inotropic effect of Angeli's salt as is illustrated by a comparison of the Ees data resulting from the combined administration of $CGRP_{8-37}$ and Angeli's salt with the results observed from administration of Angeli's salt alone. These results illustrate that the positive inotropy of HNO/NO⁻ is caused by stimulating release of CGRP, which is a nonadrenergic/noncholinergic (NANC) neuromodulator.

This is supported by the data illustrated in FIG. 7, which show that blood plasma CGRP levels were increased by administration of the HNO/NO⁻ donor Angeli's salt in both normal and heart failure conditions. A sensitive and specific radioimmunoassay (RIA) was used to study blood plasma levels of CGRP in normal and in CHF dogs, both in basal and stimulated conditions (after administration of AS, DEA/NO and nitroglycerin). The basal mean plasma levels of CGRP were 23, 24.5 and 27 pg/ml in the artery, vein, and coronary sinus of normal dogs, respectively. These levels were significantly reduced in all vascular compartments in CHF dogs: 13.3±0.7, 14.3±1.4, and 14±0.6 pg/ml in artery, vein, and sinus, respectively. When stimulated with the HNO/NO⁻ donor AS, plasma CGRP levels increased substantially in both normal and CHF dogs (FIG. 7). In contrast, stimulation with DEA/NO and nitroglycerin failed to significantly increased CGRP levels. These data clearly show that HNO/NO⁻ directly stimulates the release of CGRP.

EXAMPLE 3

This example demonstrates that HNO/NO⁻ effectively increases contractility even when administered to a subject receiving beta-antagonist therapy.

As illustrated in FIG. 8, administration of the HNO/NO⁻ donor Angeli's salt (as described in Example 1) to a normal subject that is receiving beta-antagonist therapy (propranolol, 2 milligrams/kg in bolus) caused an increase in contractility as indexed by Ees and $D_{EDV}$. This increase was observed despite the propranolol-induced reduction in myocardial performance. Similar results were obtained in one heart failure subject (data not shown).

The above-described examples merely provide particular embodiments of the provided method. They are not intended to be limiting in any way. Moreover, although embodiments of the method provided have been described herein in detail, it will be understood by those of skill in the art that variations may be made thereto without departing from the spirit of the invention or scope of the appended claims.

We claim:

1. A method of treating systolic heart failure in a subject, comprising:
   administering to the subject a therapeutically effective dose of HNO by administration of a compound that donates HNO under physiological conditions;
   wherein the HNO donating compound increases the subject's myocardial contractility; and wherein the subject is in need of myocardial contractility increases caused by primary as opposed to secondary effects.

2. The method of claim 1, wherein the subject is receiving beta-adrenergic receptor antagonist therapy.

3. The method of claim 2, wherein the HNO donating compound comprises Angeli's salt.

4. The method of claim 2 wherein the beta-adrenergic receptor antagonist is propranolol.

5. A method of increasing myocardial contractility in a subject in need thereof, comprising:
   administering to the subject a therapeutically effective dose of HNO by administration of a compound that donates HNO under physiological conditions;
   wherein the nitroxyl donating compound increases the subject's myocardial contractility; and
   wherein the subject's basal cardiovascular function is not amenable to a substantial decrease in blood pressure.

6. The method of claim 5, wherein the subject is receiving beta-adrenergic receptor antagonist therapy.

7. The method of claim 1, wherein the HNO donating compound is administered as a pharmaceutical composition suitable for infusion.

8. The method of claim 2, wherein the HNO donating compound is administered as a pharmaceutical composition suitable for infusion.

9. The method of claim 5, wherein the HNO donating compound is administered as a pharmaceutical composition suitable for infusion.

10. The method of claim 1, wherein the subject is experiencing acute heart failure.

11. The method of claim 2, wherein the subject is experiencing acute heart failure.

12. The method of claim 5, wherein the subject is experiencing acute heart failure.

13. The method of claim 2, wherein the subject is receiving beta-adrenergic receptor antagonist therapy that is selective for a particular receptor.

14. The method of claim 13, wherein the subject is receiving beta-adrenergic receptor antagonist therapy that is selective for the beta-1 receptor.

15. The method of claim 2, wherein the subject is receiving beta-adrenergic receptor antagonist therapy that is not selective for a particular receptor.

16. A method of treating systolic heart failure in a subject, comprising:
   administering to the subject a therapeutically effective dose of HNO by administration of a compound that donates HNO under physiological conditions;
   wherein the HNO donating compound increases the subject's myocardial contractility; and
   wherein the subject is in need of a positive inotropic effect without a substantial decrease in blood pressure.

17. The method of claim 16, wherein the subject is receiving beta-antagonist therapy and wherein the HNO donating compound exerts its positive inotropic effect independent of the adrenergic system.

18. The method of claim 1, 5 or 16, wherein the subject is experiencing lung congestion.

* * * * *